US005192540A

United States Patent [19]

Kuo et al.

[11] Patent Number: 5,192,540

[45] Date of Patent: Mar. 9, 1993

[54] ***HAEMOPHILUS INFLUENZAE* TYPE B OXIDIZED POLYSACCHARIDE-OUTER MEMBRANE PROTEIN CONJUGATE VACCINE**

[75] Inventors: Joseph S.-C. Kuo, Tappan; James E. Bristol, Pearl River, both of N.Y.

[73] Assignee: American Cyanamid Company, Stamford, Conn.

[21] Appl. No.: 311,873

[22] Filed: Feb. 21, 1989

Related U.S. Application Data

[63] Continuation-in-part of Ser. No. 183,206, Apr. 19, 1988, abandoned.

[51] Int. Cl.[5] ........................ A61K 39/02; C07K 3/00

[52] U.S. Cl. ........................................ 424/92; 530/324; 530/395; 530/405; 530/409; 530/412; 530/413; 536/18.7

[58] Field of Search .................. 424/92; 530/324, 395, 530/405, 409, 412, 413; 536/18.7

[56] References Cited

U.S. PATENT DOCUMENTS 4,220,717 9/1980 Kuo ........................................ 424/92

OTHER PUBLICATIONS

Munson et al, *J. Clin. Invest.* vol. 72, pp. 677–684, 1983.

Vachon et al, J. Bacteriol., vol. 162, pp. 918–924, 1985.

*Primary Examiner*—Johnnie R. Brown
*Assistant Examiner*—Abdel A. Mohamed
*Attorney, Agent, or Firm*—Alan M. Gordon

[57] ABSTRACT

Immunogenic conjugates of a 38,000 daltons or 40,000 daltons outer membrane protein of *H. influenzae* type b and oxidized polyribosyl-ribitol-phosphate polysaccharide fragments of *H. influenzae* type b are disclosed. Vaccines containing the conjugates are disclosed as useful in immunizing against *H. influenzae* type b caused disease. Method for isolating and purifying the 38,000 daltons and 40,000 daltons outer membrane proteins and for preparing the oxidized polyribosyl-ribitol-phosphate polysaccharide fragments are also disclosed.

7 Claims, 4 Drawing Sheets

*HAEMOPHILUS INFLUENZAE* TYPE B OXIDIZED POLYSACCHARIDE-OUTER MEMBRANE PROTEIN CONJUGATE VACCINE

This application is a continuation-in-part of U.S. Ser. No. 183,206, filed Apr. 19, 1988, now abandoned.

BACKGROUND OF THE INVENTION

The *Haemophilus influenzae* type b polysaccharide vaccine currently in use, which consists of the capsular polysaccharide, polyribosyl-ribitol-phosphate ("PRP"), confers immunity in children 18 months of age or older, but not in younger children, who are at greatest risk of *Haemophilus influenzae* type b caused diseases.

Attempts have been made to modify the immunological characteristics and enhance the immunogenicity of the polysaccharide by preparing polysaccharide-protein conjugate vaccines in which the PRP is coupled to a protein carrier.

The following references discuss the related art:

(1) Chu, et al., Further Studies on the Immunogenicity of *Haemophilus influenzae* Type b and Pneumococcal Type 6A Polysaccharide-Protein Conjugates, Infect. Immun., 40, 245–256, (1983), relates to the preparation of conjugates of each of *H. influenzae* type b and pneumococcal 6A polysaccharides to tetanus toxoid by a complex procedure including activation of the polysaccharide with cyanogen bromide, derivatization of the activated polysaccharide with a spacer molecule, adipic acid dihydrazide ("ADH"), and then conjugation to the protein (tentanus toxoid) with a water soluble carbodiimide to form an amido type of linkage to the protein and a complex variety of linkages from the adipic acid spacer to the polysaccharide.

(2) Jennings et al. U.S. Pat. No. 4,356,170 relates to the formation of polysaccharide-protein conjugates by the introduction of reactive aldehyde groups into the terminal residues of antigenic bacterial polysaccharides, specifically those of *E. coli*, meningococci, pneumococci, β-hemolytic streptococci and *H. influenzae*, by controlled oxidation and reacting the said aldehyde residues with the free amino groups of proteins, specifically those of tetanus toxoid, diphtheria toxoid, and immunogenic protein such as β-hemolytic streptococci, *E. coli, H. influenzae*, meningococci and pneumococci by reductive amination to covalently link said polysaccharide and protein.

(3) Anderson U.S. Pat. No. 4,673,574 relates to the formation of immunogenic conjugates comprising the reductive amination product of an immunogenic capsular polysaccharide fragment derived from the capsular polymer of *Streptococcus pneumoniae* or *H. influenzae* and containing a reducing end, prepared by means such as oxidative cleavage with periodate or by hydrolysis of a glycosidic linkage, and a bacterial toxin or toxoid as a protein carrier.

(4) Hillman et al. U.S. Pat. No. 4,459,286 relates to the preparation of a polysaccharide-protein conjugate by activation of the *H. influenzae* type b polysaccharide with cyanogen bromide, derivatization of the activated polysaccharide with a spacer molecule, 6-aminocaproic acid, and the conjugation of the major outer membrane protein of *Neisseria meninoitidis* with a water soluble carbodiimide to form an amido type of linkage to the protein and a complex variety of linkages from the 6-aminocaproic acid spacer to the polysaccharide.

(5) Gordon U.S. Pat. No. 4,496,538 relates to the production of a water-soluble covalent polysaccharide-diphtheria toxoid conjugate, wherein a pure *H. influenzae* type b polysaccharide is activated with cyanogen bromide and intimately mixed with diphtheria toxoid which has been derivatized with an ADH spacer.

(6) Munson, et al., Purification and Comparison of Outer Membrane Protein P2 from *H. influenzae* Type b Isolates, J. Clin. Invest., 72, 677–684 (1983), relates to the purification of a major outer membrane protein from *H. influenzae* type b which has an indicated molecular weight of 37,000 daltons and is designated P2. This major membrane protein is immunogenic and the antibody against P2 confers passive protection in young animals.

(7) Vachon, et. al., Transmembrane Permeability Channels across the Outer Membrane of *H. influenzae* type b, J. Bacteriol., 162, 918–924 (1985), relates to the isolation of a major protein of molecular weight 40,000 daltons ("40K") from the outer membrane of *H. influenzae* type b. The 40K protein acts as a porin in reconstituted vesicles by forming water-filled channels that allow the permeation of low molecular weight solutes.

SUMMARY OF THE INVENTION

This invention is directed to the preparation of immunogenic conjugates of an oxidized form of the capsular polysaccharide (PRP) and a major outer membrane protein of *H. influenzae* type b and the use of such conjugate(s) in vaccine(s) to confer protection against *H. influenzae* type b disease.

Among the aspects of this invention are processes for the isolation and purification of the major outer membrane proteins (P2 proteins) of *H. influenzae* type b with an indicated molecular weight of 38,000 daltons ("38K") or 40,000 daltons ("40K") using anion exchange and hydroxylapatite column chromatography. The amino acid compositions, terminal amino acid sequences and immunological reactivities of the 38K and 40K proteins have been established.

Another aspect of this invention is a process for the preparation of the oxidized capsular polysaccharide PRP ("[0]PRP") to create reactive fragments of this polysaccharide by oxidative cleavage using periodate.

Still another aspect of this invention is a process for the covalent coupling of the fragments of the polysaccharide ([0]PRP) to the protein carrier (the 38K or 40K protein) to form conjugates.

Further, this invention teaches the use in vaccines of the aforementioned conjugates.

The conjugate vaccines of this invention are highly immunogenic in the animal model. They elicit substantially higher antibody response to PRP than those reported previously. The conjugate vaccines also induce the antibody to the major protein (the 38K or 40k protein), of *H. influenzae* type b.

The immunoconjugates prepared by this invention have distinct advantages over those disclosed previously, in that the protein carrier is derived from the outer membrane protein of *H. influenzae* type b. The conjugate vaccine elicits antibodies to both PRP and the outer membrane protein from *H. influenzae* type b and confers immunity to invasive diseases caused by *H. influenzae* type b. In addition to permitting the vaccine to confer immunity in children younger than 18 months of age, the carrier protein itself may confer immunity and not merely act as a carrier for the [0]PRP. As described hereinafter, the carrier protein induced antibody response in the same animal model as [0]PRP. Finally, because the conjugate vaccine does not include the use of the *H. influenzae* type b bacterium, administration of the vaccine will not induce *H. influenzae* type b caused diseases.

BRIEF DESCRIPTION OF THE DRAWINGS

FIG. 1 depicts the analysis on SDS-PAGE of the major outer membrane proteins as follows: Lane A: Molecular weight standards (typsin inhibitor, 21K; carbonic anhydrase, 31K; ovalbumin, 45K, serum albumin, 66K; phosphorylase b, 92K); Lanes B, C, D: partially purified outer membrane proteins from *H. influenzae* b (Lederle CK strain and Lederle WK strain) and *H. influenzae* nontypable strain; Lane E: purified 40K protein from *H. influenzae* b (Lederle CK strain); Lane F: purified 38K protein from *H. influenzae* b (Lederle WK strain).

DETAILED DESCRIPTION OF THE INVENTION

Figure 2:
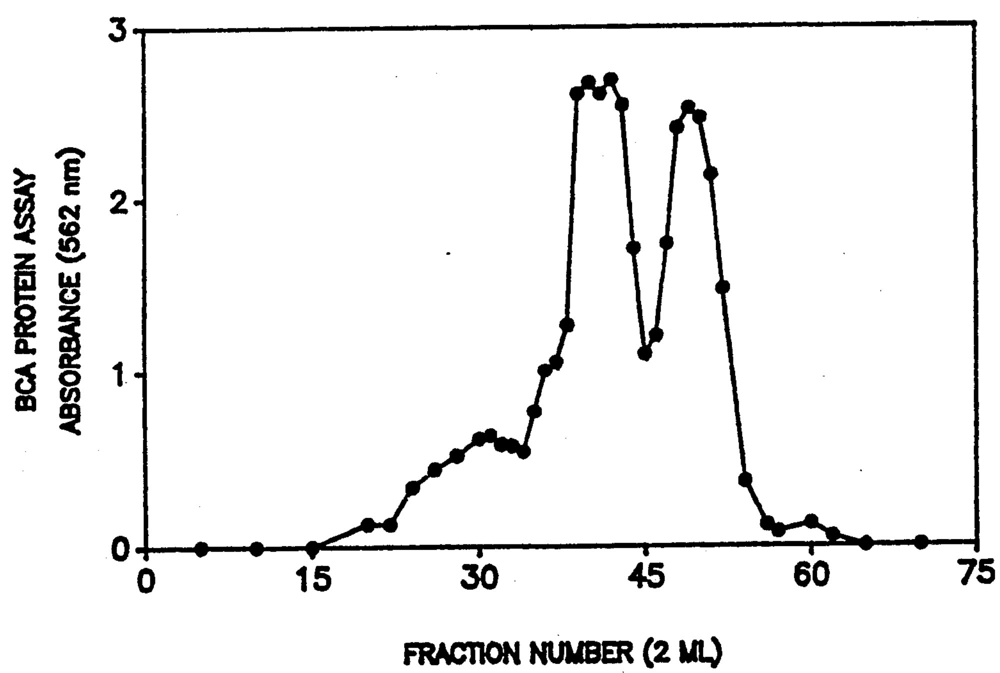
FIG. 2 depicts the results of hydroxylapatite column chromatography on a sample of the 40K protein using a 100 ml linear gradient of 50 mM to 1M sodium phosphate buffer (pH 6.5) containing 2% octyl-β-D-glucopyranoside. Fractions were monitored at 562 nm absorbance for protein content by Pierce BCA Protein Assay.

Isolation and purification of the 38K and 40K major outer membrane proteins of *H. influenzae* b The protein used in this invention is an outer membrane protein of *H. influenzae* b, whose molecular weight depends on the *H. influenzae* b strain used to produce it. Specifically, it is the major membrane protein with an indicated molecular weight of 38K or 40K on sodium dodecyl sulfate polyacrylamide gel electrophoresis ("SDS-PAGE") using the method described in Munson, et al. and Vachon, et al., supra.

The 38K protein is produced by the strain of *H. influenzae* type b designated Lederle WK, which has been deposited on Apr. 12, 1988 with the American Type Culture Collection, 12301 Parktown Drive, Rockville, Md. and has been assigned ATCC accession number 53,763. The 40K protein is produced by the strain of *H. influenzae* type b designated Lederle CK, which has been deposited on Oct. 11, 1978 with the American Type Culture Collection, 12301 Parktown Drive, Rockville, Md. and has been assigned ATCC accession number 31,441.

The 38K and 40K major outer membrane proteins are part of the group of six major outer membrane proteins that have been isolated from *H. influenzae* type b. The 38K and 40K proteins have been referred to as the P2 or b/c proteins based on their forming a discrete band during SDS-PAGE. Loeb et al., Cross-Reactivity of Surface-Exposed Epitopes of Outer Membrane Antigens of *Haemophilus influenzae* Type b, Infect. Immun., 55, 2977–2983 (1987). The molecular weights observed may vary slightly depending on the technique used in performing the analysis.

In one embodiment, the isolation and purification of the 38K or 40K dalton outer membrane protein utilizes an improved method based on that described by Blake and Gotschlich, Purification and partial characterization of the major outer membrane protein of *Neisseria gonorrhoea*, Infect. Immunol., 36, 277–283 (1982) and Vachon, et al. supra. which are incorporated by reference.

A 20 gram portion (wet weight) of *H. influenzae* b, which had been inactivated with 0.01% thimerosal, was suspended in 9 volumes of distilled water. The bacterial suspension was brought to a final concentration of 2% (w/v) hexadecyltrimethylammonium bromide and was shaken vigorously for 1 hour at 37° C. After centrifugation at 17,000×G for 30 minutes at 4° C., the pellet was removed and resuspended in 9 volumes of distilled water, followed by the addition of calcium chloride to a final concentration of 0.25M. This solution was stirred for 1 hour at room temperature and then brought to a final concentration of 20% (v/v) with ethanol. The preparation was allowed to precipitate for 3 hours at 4° C.

The precipitate was subsequently removed by centrifugation, then the protein in the supernatant was precipitated by the addition of ethanol to a final concentration of 80%. The major outer membrane protein-containing material was recovered by centrifugation at 17,000×G for 30 minutes at 4° C. and extracted with 25 mM imidazole buffer (pH 7.0) containing 0.01% thimerosal and 0.1% octyl-β-D-glucopyranoside to remove soluble contaminant PRP and nucleic acids. The major outer membrane protein-containing material was recovered by centrifugation and then solubilized in 25 mM imidazole buffer (pH 7.0) containing 2% octyl-β-D-glucopyranoside for 1 hour at room temperature. Any insoluble protein was removed by centrifugation. The supernatant, which contains the major outer membrane protein (38K or 40k), was then passed through a 1×60 cm anion exchange column of DEAE-Sephacel (Pharmacia, Inc.,Piscataway, N.J.) to remove contaminating lipopolysaccharide.

Fractions were assayed for the presence of protein using the Lowry protein assay. One hundred μl samples of fractions were used. To each sample was added one ml of a solution prepared by mixing one part of 0.5% $CuSO_4.5H_2O$ (w/v) in water with 50 parts of 2% $Na_2CO_3$ (w/v), 0.02% sodium potassium tartrate (w/v) and 0.4% NaOH (w/v) in water. After 15 minutes, 100 μl of 1N phenol reagent was added. Absorbance of the sample was measured at 750 nm using a Gilford, 260 UV-visible spectrophotometer after incubation for 20 minutes at ambient temperature. Protein concentrations were determined by comparison with a standard protein solution of bovine serum albumin. For samples containing octyl-β-D-glucopyranoside, protein was measured using the BCA Protein Assay (Pierce Chemical Co., Rockford, Ill., catalog no. 23225).

Figure 1:
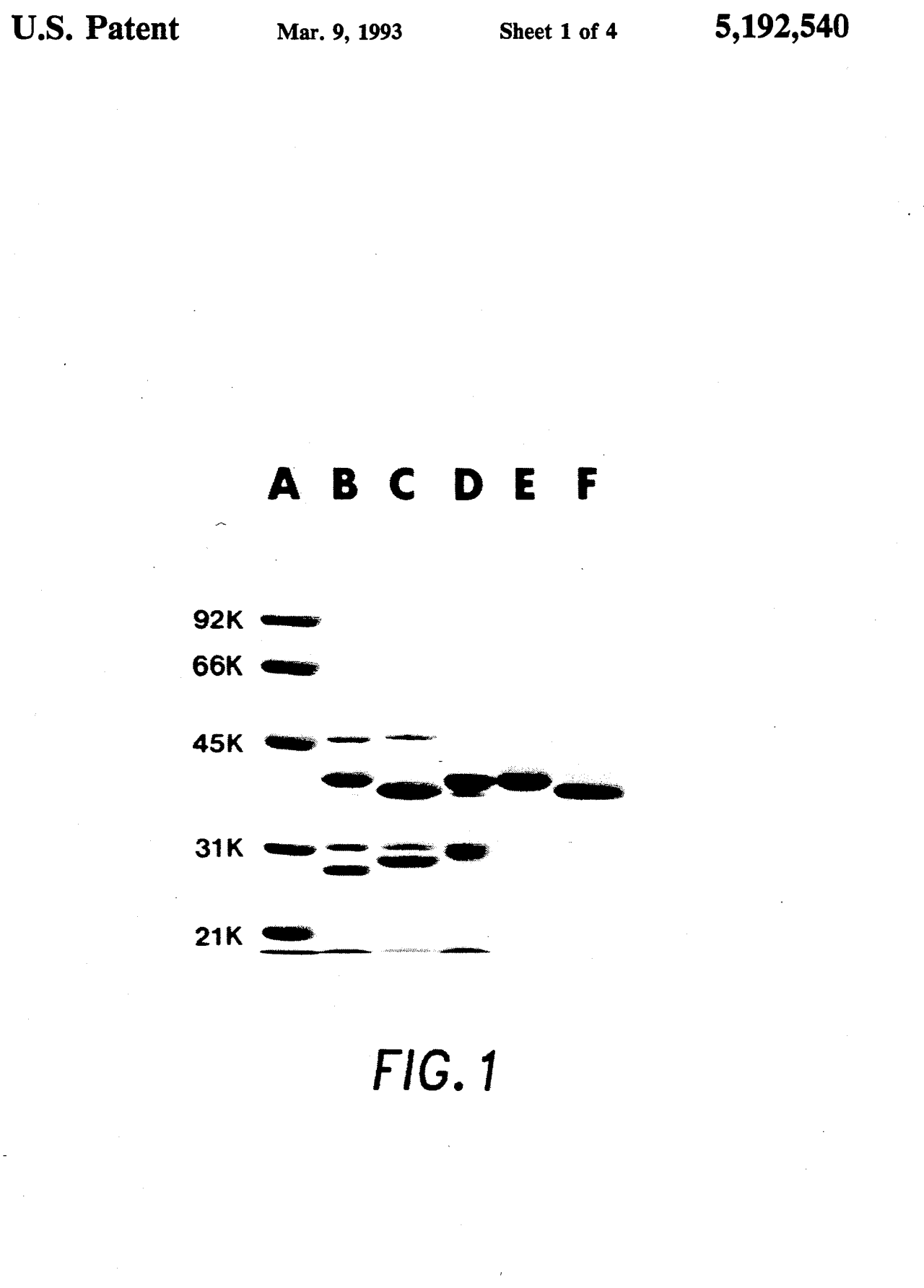

About 50% of the 38K or 40K protein was eluted from the column with imidazole buffer, pH 7.0. The remaining 50% of the 38K or 40K protein (about 20 mg) was recovered from the column by elution with 0.5M potassium chloride. FIG. 1 shows the SDS-PAGE bands corresponding to the 38K and 40K proteins compared to standards of known molecular weight.

The 40K protein purified in the manner just described was utilized in Examples 1-5 and 7 set forth below.

In an improved embodiment, the 40K protein was purified by solubilizing with sodium phosphate buffer containing octyl-β-D-glucopyranoside, followed by hydroxylapatite ("HA") column chromatography. A sample of 40K protein, which had been partially purified prior to column chromotographic purification, using the techniques described above, contained contaminating material such as lipopolysaccharide ("LPS") and PRP.

Specifically, a sample of partially purified 40K protein from *H. influenzae* type b (CK strain) was first precipitated with 2 volumes of ethanol (final concentration of ethanol was 66%) at 0°-4° C. for at least ten minutes. The sample was centrifuged at 23,000×G for 15 minutes. Virtually all of the 40K protein (>90%) was recovered in the pellet. The pellet was then dissolved in a buffer solution of either 50 mM or 200 mM sodium phosphate buffer (pH 6.5) containing 2% octyl-β-D-glucopyranoside at 8 mg protein/ml. The mixture was stirred at room temperature for 1 hour and the insoluble material was removed by centrifugation.

HA column chromatography was performed at pH 6.5, using a Bio-Gel HA column (Bio-Rad Laboratories, Richmond, Cal.). The HA column contained calcium and phosphate ions that formed the adsorption sites. The gel (40 ml) was pretreated with 50 mM sodium phosphate buffer (pH 6.5) and 2% octyl-β-D-glucopyranoside and then equilibrated with at least 2 volumes of the buffer. Subsequently, a 10 ml (80 mg) portion of the 38K or 40K protein was applied to a HA column (3×8 cm). The sample was eluted with a 100 ml linear gradient of 50 mM to 1M sodium phosphate buffer (pH 6.5) containing 2% octyl-β-D-glucopyranoside. The column eluate was collected in fractions of 2 ml per tube at a flow rate of approximately 10 ml/hour. Fractions were monitored at 562 nm absorbance for protein content by Pierce BCA Protein Assay. Fractions containing the 40K protein were pooled and were analyzed for protein concentration and purity by Pierce BCA Protein Assay and by SDS-PAGE. The LPS and PRP contents in the purified preparation were also determined.

The 40K protein was eluted from the column as two peaks (see FIG. 2) at approximately 0.45-0.5M phosphate concentration. The eluted protein was nearly homogeneous by SDS-PAGE and appeared virtually free of contaminating LPS and PRP. The protein from both peaks had a similar N-terminal sequence.

The 38K and 40K were also purified by HA chromatography with a stepwise phosphate gradient on an HA column. A sample of partially purified 40K protein from *H. influenzae* type b (CK Strain) was applied onto a column of HA and first eluted with 1.5 volumes of 0.2M phosphate (pH 6.5) and 2% octyl-β-D-glucopyranos, and then with 1.0M phosphate buffer (pH 6.5) 2% octyl-β-D-glucopyranoside. By using this procedure, the majority of the 40K protein was eluted as a single peak at a phosphate concentration of approximately 0.5-0.7M (see FIG. 3).

The stepwise phosphate gradient procedure was also used to purify a partially purified 38K protein from *H. influenzae* type b (WK Strain). The majority of the 38K protein was eluted from an HA column as a single peak at a phosphate concentration of approximately 0.5-0.7M (see FIG. 4).

Figure 3:
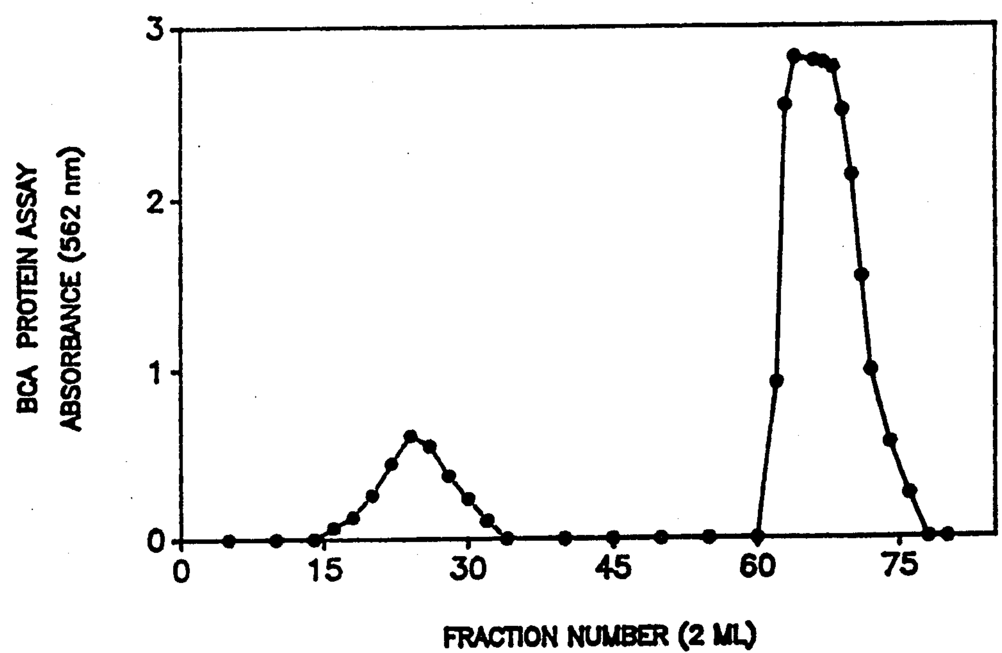
FIG. 3 depicts the results of hydroxylapatite column chromatography on a sample of the 40K protein using a stepwise phosphate gradient of (a) 0.2M phosphate buffer (pH 6.5) containing 2% octyl-β-D-glucopyranoside, then (b) 1.0M phosphate buffer (pH 6.5) containing 2% octyl-β-D-glucopyranoside. Fractions were monitored as in FIG. 2.
Figure 4:
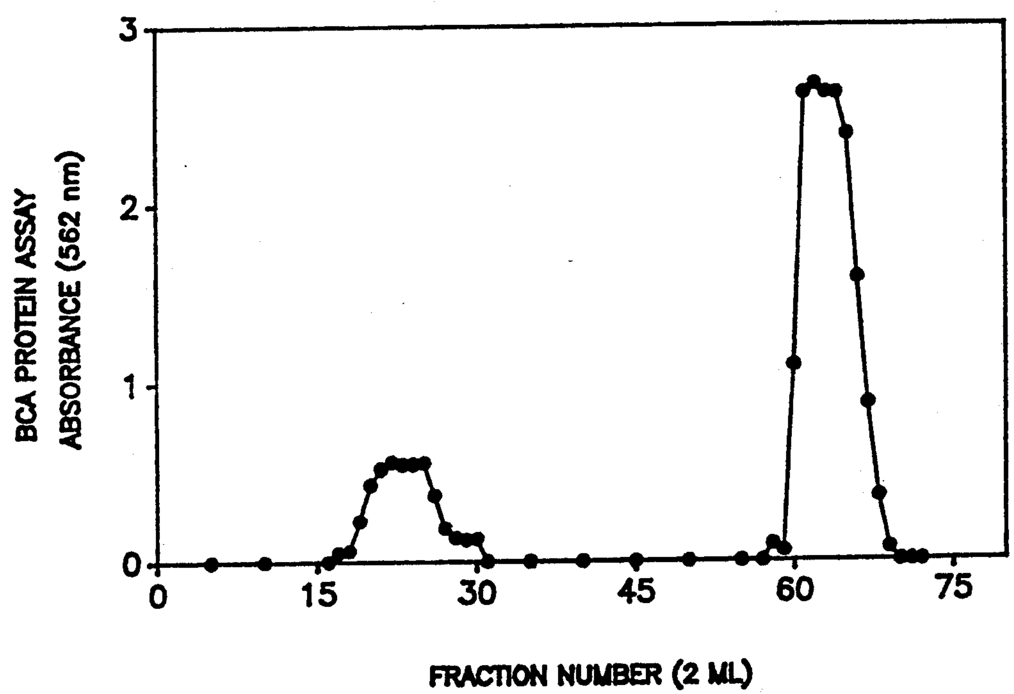
FIG. 4 depicts the results of hydroxylapatite column chromatography on a sample of the 38K protein using the stepwise phosphate gradient of FIG. 3. Fractions were monitored as in FIG. 2.

At low phosphate concentrations (200 mM), small amounts of the 38K protein or the 40K protein co-eluted with PRP (first peak in FIGS. 3 and 4). The protein-containing fractions of each protein were pooled and in both cases found to be nearly homogeneous by SDS-PAGE. Densitometric scans of each stained gel (with coomassie brilliant blue) showed that the 38K and 40K proteins purified by HA chromatography accounted for at least 90% of the total protein. This 90% or more yield of protein obtained through the use of HA chromatography is a significant improvement over the 50% yield obtained by anion exchange chromatography.

The amounts of PRP and endotoxin contents in the final preparations were very low. The final protein preparations had <1.5 μg PRP/100 μg protein and <5.0 endotoxin units/100 μg protein. They passed the rabbit pyrogen test at 2.5 μg protein/kg rabbit weight.

The purified 38K and 40K outer membrane proteins were characterized in several ways. Western blot analysis revealed that the 38K and 40K proteins were cross-reactive. Therefore, a finding that one protein would elicit an antibody response in warm-blooded animals (as shown in Example 6 below) would mean that the other protein would also elicit a cross-reactive antibody response.

An amino acid analysis was performed on a sample of each protein which had been hydrolyzed in 6N hydrochloric acid for 24 hours at 110° C., using a Beckman 121/MB amino acid analyzer. The amino acid compositions of the 38K and 40K proteins are shown in Table I.

TABLE I

Amino Acid Composition of the 40K and 38K Major Outer Membrane Proteins of *H. influenzae* b

| Amino Acid | Amino Acid Content (Mole of Residue per Mole of Protein*) 40K Protein | 38K Protein |
|---|---|---|
| Basic | 54 (0.15**) | 51 (0.15) |
| Lysine | 32 | 29 |
| Histidine | 7 | 7 |
| Arginine | 15 | 15 |
| Dicarboxylic | 89 (0.24) | 85 (0.24) |
| Aspartic, Asparagine | 47 | 45 |
| Glutamic, Glutamine | 41 | 40 |
| Neutral | 226 (0.61) | 210 (0.61) |
| Threonine | 26 | 26 |
| Serine | 16 | 13 |
| Proline | 3 | 3 |
| Glycine | 50 | 44 |
| Alanine | 27 | 25 |
| Valine | 29 | 27 |
| Methionine | 1 | 1 |
| Isoleucine | 15 | 14 |
| Leucine | 26 | 24 |
| Tyrosine | 20 | 20 |
| Phenylalanine | 13 | 13 |

*Based on indicated molecular weight of the proteins in SDS-PAGE.
**Fraction of the total moles of amino acid residues the group represents.

Amino-terminal sequence analyses were carried out on an Applied Biosystems Gas Phase Sequencer Model 470, in conjunction with PTH amino acid analysis on a Hewlett Packard Model 1090 HPLC equipped with an IBM cyano column. Carboxy-terminal amino acid sequences were determined by enzymatic methods. Digestion was accomplished by using both carboxypeptidase A and B; amino acid analyses of aliquots taken at various times were performed on a Beckman 6300 amino acid analyzer.

The amino-termini of the 38K and 40K proteins are identical, as are the carboxy-termini. The sequences are shown in Table II.

TABLE II

| Amino- and Carboxy-Terminal Sequences of 40K and 38K Protein from *H. Influenzae* b |
|---|
| Amino-Terminal Sequences for Type b 40K and 38K Protein: |
| $NH_2$-Alanine-Valine-Valine-Tyrosine-Asparagine-Asparagine-Glutamic acid-Glycine-Threonine-Asparagine-Valine-Glutamic acid-Leucine-Glycine-Glycine-Arginine-Leucine-Serine-Isoleucine-Isoleucine-Alanine-Glutamic Acid-Glutamine-Serine-Asparagine- |

Carboxy-Terminal Sequences for Type b-40K and 38K Protein

Lysine-Leucine-Phenylalanine-Valine-Arginine-Tyrosine-COOH

Preparation of *H. influenzae* b capsular polysaccharide, polyribosyl-ribitol-phosphate (PRP)

The *H. influenzae* b PRP used in this invention has been described in commonly-assigned Kuo U.S. Pat. No. 4,220,717, which is incorporated by reference. Using the procedure described in this patent, a *H. influenzae* b organism was grown in a culture, centrifuged, and the cell free supernatant collected. The supernatant was then precipitated with ethanol, the precipitate was treated with hexadecyltrimethyl ammonium bromide, and then again with ethanol to recover partially purified PRP. That PRP was then treated with hydroxylapatite, which adsorbed contaminants, so that PRP remained in the supernatant. If any further purification is necessary, the PRP may be applied to a Sepharose 4B-CL column (Pharmacia, Piscataway, N.J.). The PRP so obtained was a relatively high molecular size of PRP, with more than 50% having an elution coefficient ($K_{av}$) value less than 0.30 on a column of Sepharose 4B-CL. This value corresponds to a molecular weight greater than $1 \times 10^6$ daltons.

Preparation of PRP fragments by periodate oxidation of PRP

In its native form, PRP has no reducing ends. In order to create PRP fragments which contain reducing ends (in the form of terminal reactive aldehyde groups), the cis-vicinal hydroxyl group of the polysaccharides was oxidized by a periodate such as sodium periodate, potassium periodate or periodic acid to generate aldehyde functions following the procedure described by Parikh et al., Methods Enzymol., 34, 77-102 (1974) and Jennings et al. U.S. Pat. No. 4,356,170, both of which are incorporated by reference. The use of sodium periodate is preferred. The purified PRP was treated in the dark with 0.2-50 mM of sodium periodate at 4° C. or at room temperature, for various lengths of time. In a preferred embodiment, the PRP was treated at pH 4-7. In a particularly preferred embodiment, the PRP was treated at pH 4.0-4.5. The [0]PRP was then dialyzed extensively against pyrogen-free water to remove small molecular size materials. Alternatively, the [0]PRP may be purified through a gel filtration column [beaded agarose acrylamide copolymer (Sephacryl S-200 or S-300, Pharmacia)]. When a gel filtration column was used, fractions were assayed for the presence of [0]PRP by the orcinol reaction using D-ribose as the standard. Absorbance of fractions was measured at 672 nm. The purified product was then recovered by concentrating and drying. The resulting [0]PRP fragments had chain lengths of about 8-120 monomeric units. This chain length may also be referred to as the degree of polymerization ("D.P.") The [0]PRP was then coupled with the 38K or 40K protein by reductive amination as will now be described.

Preparation of the [0]PRP-major outer member protein conjugate

The aldehyde functions in the [0]PRP were reacted with a solution of the outer membrane protein which contains amino groups to form Schiff bases. The reaction is carried out at pH 3.5 to 9 and is preferably carried out at pH 5 to 9. These Schiff bases are then reduced with a suitable borohydride at pH 6.0-6.7 to form a stable, covalently-bonded conjugate. Examples of such borohydrides include sodium borohydride, sodium cyanoborohydride, potassium borohydride and lithium borohydride. The use of sodium cyanoborohydride is preferred. The methodology for the coupling of oxidized polysaccharide or polysaccharide fragments to a protein using borohydride has been described by Parikh et al. (supra), and Schwartz and Gray, Arch. Biochem. Biophys., 181, 542-549 (1977), which are incorporated herein by reference. The purified major protein (concentration 1-40 mg/ml) was mixed with [0]PRP (concentration 10-80 mg/ml) in 0.2M potassium phosphate buffer, pH 6.0-6.7, at room temperature. After 20-30 minutes of incubation with gentle stirring, 0.1-2.0 mM of sodium cyanoborohydride dissolved in pyrogen-free water was added.

This mixture was then incubated at 25°-37° C. with gentle stirring for 1-6 days to form the [0]PRP-outer membrane protein conjugate. The conjugate was purified on a gel filtration column such as Sephacryl S-200, S-300 or Sepharose CL-4B (Pharmacia). Fractions were assayed for protein and [0]PRP as described previously. The peak fractions which contained the conjugate were pooled, diafiltered and/or lyophilized. Alternatively, the conjugate may be purified by dialysis.

The conjugates which have been prepared and purified in accordance with this invention are preferably used in the preparation of vaccines to confer protection against *H. influenzae* type b caused diseases. The conjugates may be added to immunologically acceptable diluents or carriers in a conventional manner to prepare injectable liquid solutions or suspensions. In addition, the conjugates may be bound to aluminium hydroxide, aluminum phosphate (alum) or other pharmaceutically acceptable adjuvants.

For instance, to prepare a conjugate vaccine containing [0]PRP and the major membrane protein of *H. influenzae* b, the conjugate preparation was suspended in sodium phosphate-buffered saline ("PBS") (pH 7.0-7.4) at concentrations of 5-100 μg of PRP/ml as measured by the orcinol reaction [Herbert, et al., Methods in Microbiology, 5B, 285-291 (1971)].

The conjugate vaccines of this invention may be administered by injection in a conventional manner such as subcutaneous or intramuscular injection into warm-blooded animals to elict an active immune response for protection against systemic infection caused by the pathogen *H. influenzae* b. The dosage to be administered is determined by means known to those skilled in the art. Protection may be conferred by a single dose of vaccine, or may require the administration of several booster doses.

The following examples further illustrate the invention but are not to be construed as limiting the scope thereof. Examples 1 and 2 were performed at room temperature. The oxidation steps in Examples 3–5 were performed at 2°–8° C.; the conjugation steps in Examples 3–5 were performed at 37° C. The [0]PRP prepared had approximate D.P. values of 10 (Ex. 1), 37 (Ex. 2), 8 (Ex. 3), 40 (Ex. 4) and 120 (Ex. 5), as measured by the procedure of Park and Johnson, J. Biol. Chem. 181, 149–151 (1949) for reducing sugars.

EXAMPLE 1

Preparation of [0]PRP-40K Protein Conjugate

A 500 mg portion of PRP was dissolved in 50 ml of 0.1M sodium acetate buffer (pH 4.5). A 107 mg portion of sodium periodate was added in the dark and the mixture was stirred gently for 30 minutes in a capped brown glass bottle wrapped in aluminum foil. The excess sodium periodate was destroyed by the addition of 500 μl of 3M ribitol solution and gentle stirring for 10 minutes. The reaction mixture containing the resulting [0]PRP was extensively dialyzed against pyrogen-free water in a Spectropor ® membrane tubing (Spectrum Medical Industries, Inc., Los Angeles, Cal.) with 3.5K (M.W.) cut-off for 3 days at 4° C., using 2 liters of fresh water each day. The dialyzed [0]PRP was then filtered through a 0.2μ Nalge filter, lyophilized and stored at 4° C. The [0]PRP had a D.P. value of approximately 10. The [0]PRP was found to elute with a $K_{av}$ value of about 0.5 from a column of Sephacryl S-200. The recovery of [0]PRP from the PRP preparation was approximately 50%.

The 40K membrane protein was concentrated using an Amicon concentrator (10K (M.W.) cut-off filter) with 0.2M potassium phosphate buffer (pH 6.5) plus 2% octyl-β-D-glucopyranoside to a protein concentration of about 20 mg/ml. An 80 mg portion of [0]PRP was dissolved in 4 ml of the 40K membrane protein solution with gentle stirring. After 20 minutes, 0.5 mM of sodium cyanoborohydride was added and this mixture was incubated at room temperature with gentle stirring for 3 days. The mixture was chromatographed on a column of Sephacryl S-200 which had been equilibrated with 0.2M ammonium acetate (pH 7.0) plus 1% octyl-β-D-glucopyranoside. The first peak fractions containing the conjugate were pooled and used for the preparation of the vaccine. The [0]PRP-40K protein conjugate had a PRP/protein (w/w) ratio of about 1:2.5.

EXAMPLE 2

Preparation of [0]PRP-40K Protein Conjugate

A 500 mg portion of PRP was dissolved in 50 ml of 0.1 M sodium acetate buffer (pH 4.5). A 21.4 mg portion of sodium periodate was added in the dark and the mixture was stirred gently for 30 minutes in a capped brown glass bottle wrapped in aluminum foil. The excess sodium periodate was destroyed by reaction with 500 μl of 3M ribitol for 10 minutes. The reaction mixture containing the resulting [0]PRP was extensively dialyzed against pyrogen-free water in a Spectrapor ® membrane tubing with 12K (M.W.) cut-off for 3 days at 4° C. The dialyzed [0]PRP was then filtered through a 0.2μ Nalge filter, lyophilized and then stored at 4° C. This [0]PRP had a D.P. value of approximately 37. The [0]PRP was found to elute with a $K_{av}$ value of about 0.5–0.6 from a column of Sephacryl S-300. The recovery of [0]PRP from the PRP preparation was approximately 68%.

The 40K membrane protein was concentrated using an Amicon concentrator (10K M.W. cut-off filter) with 0.2M potassium phosphate buffer (pH 6.5) plus 2% octyl-β-D-glucopyranoside to a protein concentration of about 16 mg/ml. A 40 mg portion of [0]PRP was dissolved in 1 ml of the 40K protein solution with gentle stirring. After 20 minutes, 0.5 mM of sodium cyanoborohydride was added and the mixture was incubated with gentle stirring at room temperature for 3 days. The mixture was chromatographed on a column of Sephacryl S-300 which had been equilibrated with 0.2M ammonium acetate (pH 7.0) plus 1% octyl-β-D-glucopyranoside. The conjugate material was eluted with the same buffer. Peak fractions containing the conjugate were pooled, characterized and used for the vaccine preparations. The recovery of the [0]PRP and the membrane protein in the conjugate were about 20% and 60% respectively. The [0]PRP-40K membrane protein conjugate had a PRP/protein ratio of about 1:2.

EXAMPLE 3

Preparation of [0]PRP-40K Protein Conjugate

All reactions were performed at 2°–8° C. unless otherwise stated.

A 300 mg portion of PRP was dissolved in 30 ml of pyrogen-free water, then 24 ml of cold 0.2M sodium acetate buffer (pH 4.0) was added, followed by addition of 6 ml of a 50 mg/ml solution of sodium periodate in sodium acetate buffer (pH 4.0). The final solution was 23.4 mM sodium periodate and 5 mg/ml PRP. The mixture was then incubated in the dark, in a capped bottle wrapped in aluminum foil, in an ice-water bath for 30 minutes. The excess sodium periodate was destroyed by reaction with 90 μl of 16.7M ethylene glycol for 10 minutes. The mixture was then extensively dialyzed at 4° C. in a Spectrapor ® membrane tubing with 3.5K (M.W.) cut-off, first against sterile PBS (4 liters, 2 changes, 18 hours/change), then against pyrogen-free water (same regimen). The dialyzed [0]PRP was then transferred to a container and stored at −20° C. until used for the preparation of the conjugate. This [0]PRP had a D.P. value of approximately 8. The [0]PRP was found to elute with a $K_{av}$ value of about 0.9 on Sepharose 4B-CL. A 100 mg portion of the [0]PRP in pyrogen-free water, at a concentration of 5 mg/ml was placed into a Spectrapor ® membrane tubing having a M.W. cut-off of 3.5K and reequilibrated by dialysis against 1 liter of 0.2M potassium phosphate buffer (pH 6.7) containing 1% octyl-β-D-glucopyranoside. The [0]PRP was then concentrated by placing the dialysis tubing in a shallow container filled with dried polyethylene glycol. The final [0]PRP concentration was adjusted to approximately 33 mg/ml with 0.2M potassium phosphate buffer (pH 6.7).

To 100 mg (ca. 3.0 ml) of the [0]PRP solution was added 1.3 ml of 40K protein solution (1.53 mg/ml) in phosphate buffer containing 1% octyl-β-D-glucopyranoside and 37 μl of sodium cyanoborohydride (1 mg/μl). The final volume was adjusted to 5 ml with phosphate buffer containing 1% octyl-β-D-glucopyranoside. This mixture was incubated with gentle stirring at 37° C. for 5 days. The conjugate was purified by extensive dialysis against phosphate buffered saline at 4° C. (4 liters, 2 changes, 18 hours/- change) during which the conjugate precipitated and was collected by centrifugation. The pellet was then dissolved in 0.2M potassium phosphate buffer (pH 6.7) containing 1% octyl-β-D-glucopyranoside, characterized by SDS-PAGE and used in the animal experiments described hereinafter. The [0]PRP-40K membrane protein conjugate had a PRP/protein ratio of about 1:4.

EXAMPLE 4

Preparation of [0]PRP-40K Protein Conjugate

All reactions were performed at 2°-8° C. unless otherwise stated.

A 300 mg portion of PRP was dissolved in 30 ml of pyrogen-free water. A 29.4 ml portion of cold 0.2M sodium acetate buffer (pH 4.0) was added, followed by addition of 0.6 ml of a 50 mg/ml solution of sodium periodate in sodium acetate buffer (pH 4.0). The final solution was 2.34 mM sodium periodate and 5 mg/ml PRP. This mixture was then incubated in a capped bottle wrapped in aluminum foil, in the dark, in an ice water bath for 30 minutes. The excess sodium periodate was destroyed by reaction with 90 μl of 16.7M ethylene glycol for 10 minutes. The reaction mixture containing the resulting [0]PRP was then extensively dialyzed in a Spectrapor ® membrane tubing with 3.5K (M.W.) cut-off, first against sterile PBS (4 liters, 2 changes, 18 hours/change), then against pyrogen-free water (same regimen). The dialyzed [0]PRP was then transferred to a container and stored at −20° C. until used for preparation of the conjugate. The [0]PRP had a D.P. value of about 40. The [0]PRP was found to elute with a $K_{av}$ of about 0.5–0.7 on Sepharose 4B-CL. A 100 mg portion of the [0]PRP in pyrogen-free water at a concentration of 5 mg/ml was placed in a Spectrapor ® membrane tubing having a M.W. cut-off of about 3500 daltons and reequilibrated by dialysis for 8 hours at room temperature against 1 liter of 0.2M potassium phosphate buffer (pH 6.7) containing 1% octyl-β-D-glucopyranoside. The [0]PRP was then concentrated by placing the dialysis tubing in a shallow container filled with dried polyethylene glycol. The final [0]PRP concentrate was adjusted to approximately 33 mg/ml with 0.2M potassium phosphate buffer (pH 6.7).

To 100 mg (ca. 3.0 ml) of the [0]PRP was added 1.3 ml of the 40K protein solution (1.53 mg/ml) in phosphate buffer containing 1% octyl-β-D-glucopyranoside and 37 μl of sodium cyanoborohydride (1 mg/μl). The final volume was adjusted to 5 ml with phosphate buffer containing 1% octyl-β-D-glucopyranoside and the mixture was incubated with gentle stirring for 5 days at 37° C. The mixture was then chromatographed on a column of Sephacryl S-300 which had been equilibrated with 0.2M ammonium acetate (pH 7.0). The conjugate was eluted at the void volume with the same buffer. The peak fractions were pooled, characterized and used for the vaccine preparations. The [0]PRP-40K membrane protein conjugate had a PRP/protein ratio of about 1:2.

EXAMPLE 5

Preparation of [0]PRP-40K Protein Conjugate

All reactions were performed at 2°-8° C. unless otherwise noted.

A 300 mg portion of PRP was dissolved in 30 ml of pyrogen-free water. A 29.94 ml portion of 0.2M sodium acetate buffer (pH 4.0) was added, followed by addition of 0.06 ml of sodium periodate (50 mg/ml) in sodium acetate buffer (pH 4.0). The final solution was 0.234 mM sodium periodate and 5 mg/ml PRP. This mixture was incubated in the dark, in a capped bottle wrapped in aluminum foil, in an ice-water bath for 30 minutes. The excess sodium periodate was destroyed by reaction with 90 μl of 16.7M ethylene glycol for 10 minutes. The mixture containing the resulting [0]PRP was then extensively dialyzed at 4° C. in a Spectrapor ® membrane tubing with 3.5K (M.W.) cut-off, first against sterile PBS (4 liters, 2 changes, 18 hours/change), then against pyrogen-free water (same regimen). The [0]PRP had a D.P. value of about 120. The [0]PRP was found to elute with a $K_{av}$ value of about 0.3–0.6 on Sepharose 4B-CL. A 100 mg portion of the [0]PRP in pyrogen-free water (5 mg/ml) was placed in a Spectrapor ® membrane tubing having a M.W. cut-off of 3.5K and reequilibrated by dialysis for 8 hours at room temperature against 1 liter of 0.2M potassium phosphate buffer (pH 6.7) containing 1% octyl-β-D-glucopyranoside. The [0]PRP was then concentrated by placing the dialysis tubing in a shallow container filled with dried polyethylene glycol. The final [0]PRP concentration was adjusted to approximately 33 mg/ml with 0.2M potassium phosphate buffer (pH 6.7).

To a 100 mg portion (ca. 3.0 ml) of the [0]PRP solution was added 1.3 ml of the 40K protein solution (1.53 mg/ml) in phosphate buffer containing 1% octyl-β-D-glucopyranoside and 37 ml of sodium cyanoborohydride (1 mg/ml). The final volume was adjusted to 5 ml with phosphate buffer containing 1% octyl-β-D-glucopyranoside and the mixture was incubated with gentle stirring for 5 days at 37° C. The mixture was chromatographed on a column of Sepharose 4B-CL which had been equilibrated with 0.2M ammonium acetate (pH 7.0). The conjugate was eluted with the same buffer. The peak fractions were pooled, characterized and used for the vaccine preparations. The [0]PRP-40K membrane protein conjugate had a PRP/protein ratio of about 2:1.

EXAMPLE 6

Preparation of [0]PRP-38K Protein Conjugate

A one gram portion of PRP was dissolved in 100 ml of 0.1M sodium acetate buffer (pH 4.5). A 107 mg portion of sodium periodate was added in the dark and the mixture was stirred gently for 30 minutes in a capped brown glass bottle wrapped in aluminum foil. The excess sodium periodate was destroyed by the addition one ml of 3M ribitol solution and gentle stirring for 10 minutes. The reaction mixture containing the resulting [0]PRP was extensively dialyzed against pyrogen-free water in a Spectropor, membrane tubing with 3.5K (M.W.) cut-off for 3 days at 4° C. The dialyzed [0]PRP was then filtered through a 0.2μ Nalge filter, lyophilized and stored at 4° C. The [0]PRP had a D.P. value of approximately 35. The [0]PRP was found to elute with a $K_{av}$ value of about 0.5 from a column of Sephacryl S-300. The recovery of [0]PRP from the PRP preparation was approximately 78%.

The purified 38K protein was concentrated with an Amicon concentrator using 0.2M potassium phosphate buffer (pH 6.5) plus 2% octyl-β-D-glucopyranoside to a protein concentration of about 10 mg/ml. A 30 mg portion of [0]PRP was dissolved in 3 ml of the 38K protein solution (30 mg protein) with gentle stirring. After 20 minutes, 0.3 ml of sodium cyanoborohydride (30 mg/0.3 ml water) was added and this mixture was incubated at 37° C. (shaking water bath) with gentle swirling for 3 days. The reaction material was diluted with 2% octyl-β-D-glucopyranoside (in water) to a protein concentration of approximately 2 mg/ml and extensively dialyzed against 50 mM NaCl buffer without detergent in a Spectropor membrane tubing with a M.W. cut-off of 3.5K for 2 days at 4° C., using 50 mM NaCl (500 ml) and two changes. The dialyzed material was centrifuged at 12,000×G for 10 minutes to remove insoluble material. The supernatant (5-15 ml) was applied to a column of Sepharose 4B-CL (1.5×90 cm) pre-equilibrated with 50 mM NaCl and eluted with the same buffer. Two distinct peaks were obtained for [0]PRP; the [0]PRP-38K protein conjugate was eluted at $V_0$. The peak fractions which contained the conjugate (PRP and protein) were pooled and stored at 4° C. until use. The [0]PRP-38K membrane protein conjugate had a PRP/protein ratio of about 1:5.

EXAMPLE 7

Antibody Response to Conjugate Vaccines

The conjugates prepared by the procedures of Examples 1-5 were diluted in sterile PBS at pH 7.0, such that a 0.5 ml dose contained 5 or 10 μg of PRP. The conjugate vaccines were sterilized by membrane filtration through a 0.20μ Gelman filter. The sterile vaccine was stored at 4° C. until needed.

The conjugate vaccine (0.5 ml per dose) was injected subcutaneously into young rats once each week for three weeks.

Table III sets forth the antibody response to PRP of vaccines made from the conjugates of Examples 1-5 hereto in comparison to PBS (as a control), PRP alone and two known conjugates. Table IV sets forth the antibody response to the 40K protein after receiving vaccines made from the conjugates of Examples 1, 3 and 4 hereto in comparison to PBS (as a control).

immunizations. The rats injected with the conjugates containing diptheria toxoid as a protein carrier had increased levels of the antibodies. Rats injected with the conjugate vaccine consisting of [0]PRP and 40K protein had an excellent antibody response as shown by significantly higher levels of antibodies to PRP (Table III) and to the 40K protein (Table IV).

TABLE III

Antibody Response of Young Rats to [O]PRP-40K Membrane Protein Conjugate

| Vaccine | Dose μg PRP/0.5 ml | GMT Antibody to PRP(ng/ml)* WEEKS POST ADMINISTRATION 4 | 5 |
|---|---|---|---|
| PBS (Control) | — | <40 | <40 |
| PRP | 10 | <40 | <40 |
| PRP (ADH)-Diphtheria toxoid conjugate** | 5 | 2505 | 2273 |
| | 10 | 1562 | 1119 |
| [O]PRP-Diphtheria toxoid conjugate | 5 | 189 | 114 |
| | 10 | 1474 | 655 |
| [O]PRP-40K Protein Conjugate | | | |
| Example 1 (D.P. = 10) | 5 | 50617 | 46900 |
| | 10 | 21585 | 19920 |
| Example 2 (D.P. = 37) | 5 | 18425 | 32004 |
| | 10 | 18059 | 33677 |
| Example 3 (D.P. = 8) | 5 | 4148 | 4140 |
| | 10 | 2347 | 3814 |
| Example 4 (D.P. = 40) | 5 | 69199 | 93581 |
| | 10 | 49355 | 58730 |
| Example 5 (D.P. = 120) | 5 | 19585 | 20411 |
| | 10 | 23263 | 18486 |

*Five rats per group were injected with vaccine. The geometric-mean titer (GMT) of antibody was computed from the five discrete titers.

**This conjugate consists of PRP (ADH)-diphtheria toxoid prepared by the procedure of Chu, et al., Inf. Immun., 40, 245-256 (1983). The PRP is coupled to the diphtheria toxoid through the spacer adipic dihydride (ADH) using cyanogen bromide and water soluble carbodiimide.

TABLE IV

Antibody Level to the 40K Protein in Young Rats After Receiving [O]PRP-40K Protein Conjugate

| Vaccine | Dose (0.5 ml) μg PRP | μg protein | Rat No. | Serum Antibody Titers* ($A_{492}$ at 1:320 dilution) |
|---|---|---|---|---|
| PBS (Control) | — | — | 1 | 0.380 |
| | | | 2 | 0.391 |
| | | | 3 | 0.450 |
| [O]PRP-40K Protein Conjugate | | | | |
| Example 1 (D.P. = 10) | 5 | 12.5 | 8 | 1.357 |
| | 5 | 12.5 | 9 | 1.626 |
| | 10 | 25 | 10 | 1.238 |
| | 10 | 25 | 11 | 1.343 |
| Example 3 (D.P. = 8) | 5 | 20 | 4 | 1.402 |
| | 5 | 20 | 5 | 1.186 |
| | 10 | 40 | 6 | 1.176 |
| | 10 | 40 | 7 | 1.280 |
| Example 4 (D.P. = 40) | 5 | 10 | 12 | 1.183 |
| | 5 | 10 | 13 | 0.703 |
| | 10 | 20 | 14 | 1.082 |
| | 10 | 20 | 15 | 0.677 |

*Fourth week post initial injection.

The radioimmunoassay (RIA) method used for the measurement of PRP antibody is described by Kuo, et al., J. Immunol. Methods., 43, 35-47 (1981) which is incorporated herein by reference.

The 40K protein antibody was determined by the enzyme-linked immunosorbent assay of Voller, et al., Lancet, 1, 469 (1975).

The results in Tables III and IV show that rats injected with PRP alone showed no significant increase in the PRP antibody level over the control sera after three immunizations.

We claim:

1. An immunogenic polysaccharide-protein conjugate comprising the reductive amination product of (a) an oxidized polyribosyl-ribitol-phosphate polysaccharide fragment derived from the capsular polysaccharide of *Haemophilus influenzae* type b, and (b) the outer membrane protein of *Haemophilus influenzae* type b having a molecular weight of, about, 38,000 daltons or 40,000 daltons as determined by SDS-PAGE.

2. The conjugate of claim 1, wherein the protein of *Haemophilus influenzae* type b is the major outer membrane protein of the organism.

3. The conjugate of claim 1, wherein the 38,000 daltons or 40,000 daltons outer membrane protein of *Haemophilus influenzae* type b has the N-terminal amino acid sequence $NH_2$-alanine-valine-valine-tyrosine-asparagine-asparagine-glutamic acid-glycine-threonine-asparagine-valine-glutamic acid-leucine-glycine-glycine-arginine-leucine-serine-isoleucine-isoleucine-alanine-glutamic acid-glutamine-serine-asparagine-.

4. A vaccine comprising the immunogenic conjugate of claim 1.

5. The vaccine of claim 4 which further comprises one or more of an immunologically acceptable diluent, carrier or adjuvant.

6. A method of eliciting antibody response to the polyribosyl-ribitol-phosphate polysaccharide and the 38,000 daltons and 40,000 daltons outer membrane protein of *Haemophilus influenzae* type b in warm-blooded animals, which comprises administering to said animals an immunogenic amount of the vaccine of claim 4.

7. A method of immunizing against *Haemophilus influenzae* type b caused disease in warm-blooded animals, which comprises administering to said animals the vaccine of claim 4 in an immunogenic amount by intramuscular or subcutaneous injection.

* * * * *